United States Patent [19]

Chin et al.

[11] Patent Number: 4,543,819

[45] Date of Patent: Oct. 1, 1985

[54] VAPOR-LIQUID RATIO ANALYZER

[75] Inventors: Thomas G. Chin; Arthur Alston, both of El Cerrito, Calif.

[73] Assignee: Chevron Research Company, San Francisco, Calif.

[21] Appl. No.: 543,446

[22] Filed: Oct. 19, 1983

[51] Int. Cl.⁴ ............................................... G01N 7/14
[52] U.S. Cl. .................................................... 73/64.2
[58] Field of Search ........................... 73/64.2, 61.3, 53

[56] References Cited

U.S. PATENT DOCUMENTS

| | | | |
|---|---|---|---|
| 3,145,561 | 8/1964 | Thompson | 73/64.2 |
| 3,276,460 | 10/1966 | Feld | 73/64.2 X |
| 3,491,585 | 1/1970 | Hass | 73/53 |
| 3,528,439 | 9/1970 | Plucker | 73/64.2 X |
| 3,528,440 | 9/1970 | Plucker | 73/64.2 X |
| 3,686,924 | 8/1972 | Ludt et al. | 73/53 |
| 3,813,925 | 6/1974 | Fenske et al. | 73/64.2 |
| 4,393,689 | 7/1983 | Renon et al. | 73/64.2 |

Primary Examiner—Stewart J. Levy
Assistant Examiner—Joseph W. Roskos
Attorney, Agent, or Firm—Burns, Doane, Swecker & Mathis

[57] ABSTRACT

The vapor-liquid ratio temperature of a liquid is determined for a specified vapor-liquid ratio and pressure by filling a chamber with a unit volume of the liquid. The capacity of the chamber is then expanded to generate a number of unit volumes of vapor equal to the specified ratio. Alternatively, a unit volume of the liquid can be discharged into an evacuated chamber having a fixed capacity equal to the number of unit volumes. The temperature of the liquid and vapor is maintained constant, and their pressure is measured when equilibrium is established. Deviations of the measured pressure from the specified pressure are translated into the vapor-liquid ratio temperature. In a gasoline blending environment, this temperature can be used to control the proportion of butane in the blended product.

21 Claims, 12 Drawing Figures

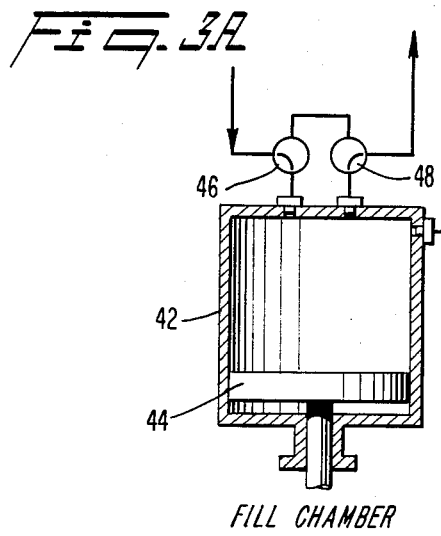
*FILL CHAMBER*
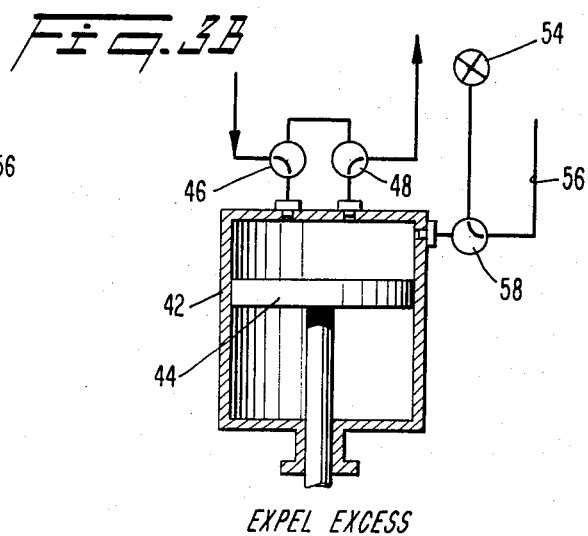
*EXPEL EXCESS*
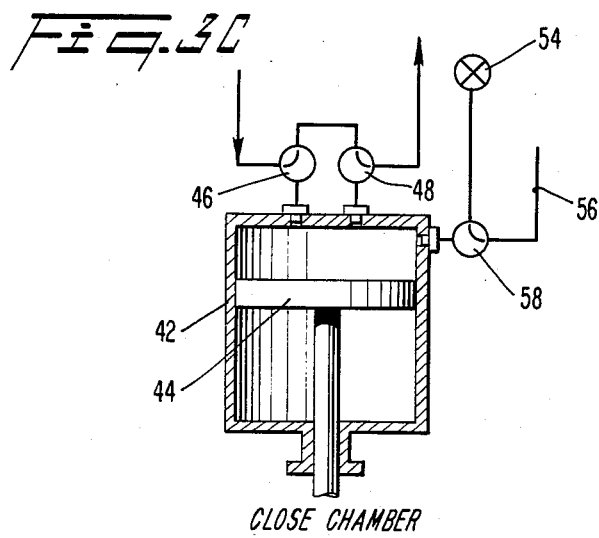
*CLOSE CHAMBER*
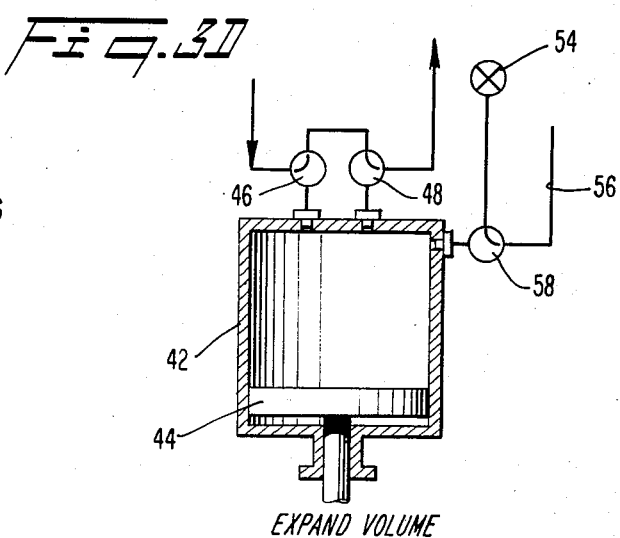
*EXPAND VOLUME*
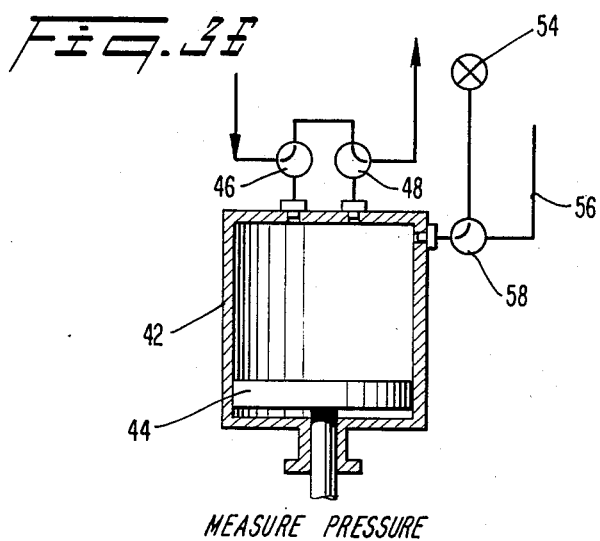
*MEASURE PRESSURE*
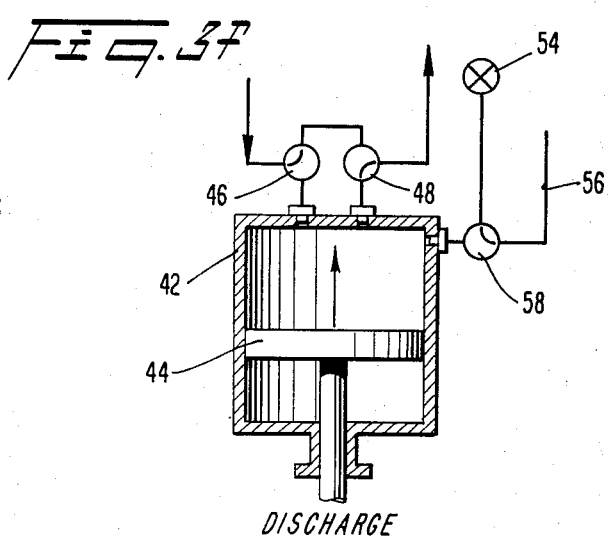
*DISCHARGE*

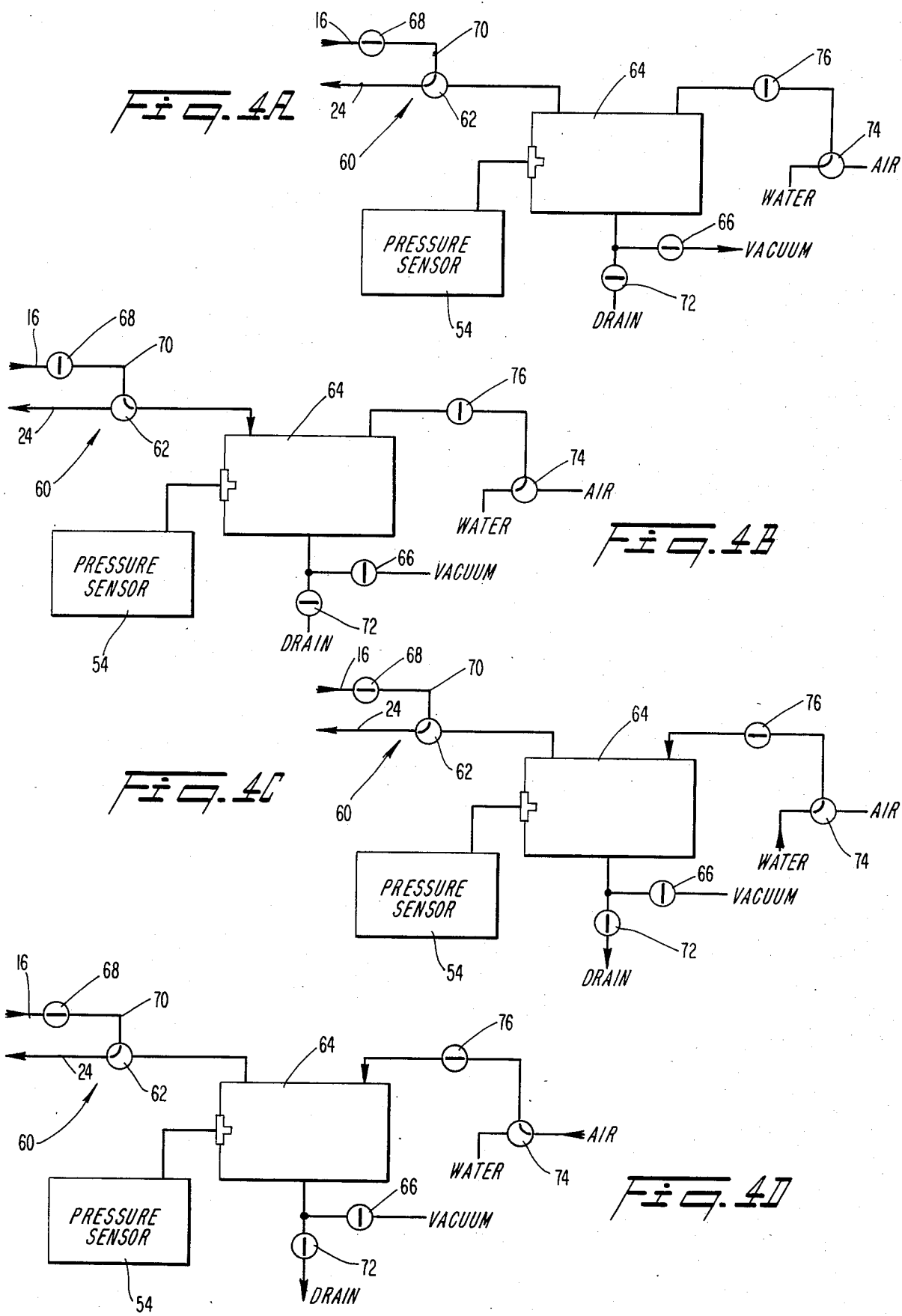

VAPOR-LIQUID RATIO ANALYZER

BACKGROUND OF THE INVENTION

The present invention is directed to an analyzer for automatically measuring the vapor-liquid ratio of a fluid, and particularly to an on-line analyzer that can be used to control the addition of volatile liquids in blended gasoline products.

In the production of blended gasoline products, various additives are blended with the refined gasoline stock to impart certain desired properties to the final product. For example, these additives can include corrosion inhibitors and anti-knock preparations. Another component which is typically added to gasoline products is a liquid having high volatility, such as butane or natural gasoline. It is necessary to impart a certain degree of volatility to the blended gasoline product, to improve the properties that affect the cold starting of engines. In addition, it is further desirable to add as much butane to the gasoline product as feasible. Since butane is much less expensive than gasoline, the more butane that is added to the blended gasoline contributes to a greater reduction in the overall cost of the final product.

However, the amount of butane that can be added to the blended gasoline product is limited due to its high volatility. If the volatility of the blended gasoline is too high, vapor lock can occur at elevated temperatures, such as those that are encountered under the hood of a vehicle. When vapor lock occurs, the supply of liquid fuel to the engine is blocked and the engine stalls until the temperature can be reduced and the evaporated gasoline condenses.

During blending, the vapor-liquid ratio (V/L) of a blended gasoline product is monitored to indicate the amount of butane that can be safely added to the product. Basically, the vapor-liquid ratio is a measurement of the relative volumes of vapor and liquid of the product that exist under equilibrium conditions at a specified temperature and pressure. In gasoline products, a vapor-liquid ratio of twenty is generally accepted as the ratio where vapor lock begins. In the blending of gasoline, a controlling parameter is not so much the actual vapor-liquid ratio of the gasoline, but rather the temperature at which a vapor-liquid ratio of twenty exists for a specified pressure. This temperature will determine the climatic conditions under which the gasoline will be suitable for use. Thus, the gasoline producer is typically concerned with blending the gasoline so that it has a specified minimum vapor-liquid ratio temperature, which temperature is associated with the particular geographic area and the time of year in which the gasoline is to be distributed.

In the past, the vapor-liquid ratio of a blended gasoline product was estimated from correlations based on the Reid vapor pressure of the gasoline and other test parameters established through standard test methods approved by the American National Standards Institute. However, there are a number of limitations associated with such estimates. Every estimate includes an unknown correlation error. The magnitude of this correlation error is dependent upon the composition of the blended product, and therefore varies almost continuously during blending since the composition of the product changes. In addition, every estimate includes the errors that are generated from the separate measurements of the Reid vapor pressure and the ASTM test parameters. Errors in the measurement of the Reid vapor pressure in particular can be large and hard to evaluate with particularity.

Accordingly, there is a need for an analyzer that can directly measure the vapor-liquid ratio of a liquid at a temperature and pressure of interest. One known type of analyzer that performs such a function is disclosed in U.S. Pat. No. 3,491,585. The analyzer disclosed in this patent operates in a continuous fashion, wherein a stream of a liquid to be tested is heated to a temperature so that the volatile constituents of the liquid become vaporized. The liquid and vapor components are then separated, and their respective flow rates are compared to one another to determine the vapor-liquid ratio of the liquid.

While an analyzer of the type disclosed in the '585 patent is commercially available, it is not known to be in wide use. Part of the reason for its lack of acceptance is due to its relatively high price. Furthermore, it is a rather complex system and accordingly is difficult to keep operational at a satisfactory level. In addition, it provides data in the form of the absolute vapor-liquid ratio, rather than the temperature for a ratio equal to 20, which is a parameter that is better understood and utilized by blenders.

Other continuously operating types of vapor-liquid ratio measuring systems are disclosed in U.S. Pat. Nos. 3,276,460; 3,686,924; 3,735,634 and 3,813,925. As far as is known, none of these systems are presently in use. It appears that they suffer from the same complexity as that of the '585 patent, and for this reason they may not be suited for practical use.

In addition to the continuously operating analyzers, vapor-liquid ratio measuring systems that operate in batch mode are also known. Representative of U.S. Patents disclosing these type of systems are U.S. Pat. Nos. 3,145,561; 3,528,439 and 3,528,440. It appears that these systems also are relatively complex, and it is believed that none of them are being used at this time.

OBJECTS AND BRIEF STATEMENT OF THE INVENTION

Accordingly, it is an object of the present invention to provide a novel method and apparatus for analyzing the vapor-liquid ratio of a blended liquid product that is simple in both construction and operation, and hence reliable.

It is another object of the present invention to provide a vapor-liquid ratio analyzer that indicates the vapor-liquid ratio temperature of a product, so that it is readily adapted for practical use in a gasoline blending environment.

It is a further object of the present invention to provide a system for controlling the addition of butane or other highly volatile products to a blended gasoline product through the on-line use of the novel vapor-liquid ratio temperature analyzer.

In accordance with the present invention, these and other objects and advantages are achieved by taking one volume of liquid and generating a volume of vapor at a specified temperature. This vapor volume is a multiple of the liquid sample volume in accordance with the desired vapor-liquid ratio, e.g. 20. The specified temperature is determined according to the temperature characteristics of the geographic area in which the product is to be distributed. The vapor pressure of the sample liquid remaining after the vapor volume has been generated, and an equilibrium condition is established, is a measure of how much the sample deviates from a specified vapor-liquid temperature. More specifically, pressure deviations from atmospheric are inversely proportional to temperature deviations from the specified temperature. For example, if the measured pressure is less than atmospheric, an indication is obtained that the vapor-liquid ratio temperature is greater than the specified temperature. Thus, the pressure measurement that is obtained, or the temperature deviation that is derived therefrom, can be used to control the addition of highly volatile liquids to the blended product, either manually or automatically, to maintain the desired vapor-liquid ratio temperature.

Further features and advantages of the present invention are explained in detail hereinafter with reference to a preferred embodiment of the invention illustrated in the accompanying drawings.

BRIEF DESCRIPTION OF THE DRAWINGS

FIGS. 3A–3F are schematic diagrams representing the sequence of steps that take place in the operation of the vapor-liquid ratio analyzer of FIG. 2; and FIGS. 4A–4D are schematic diagrams representing the operating sequence of an alternative embodiment of the invention.

DESCRIPTION OF THE PREFERRED EMBODIMENTS

In the following description of preferred embodiments of the invention, particular reference is made to the blending of gasoline and the addition of butane to the product, to facilitate an understanding of the invention. However, it will be appreciated by those having familiarity with this technology that the practical applications of the invention are not so limited. Rather, the invention can find usefulness in almost any situation in which it is desired to determine the vapor-liquid properties of a fluid.

Figure 1:
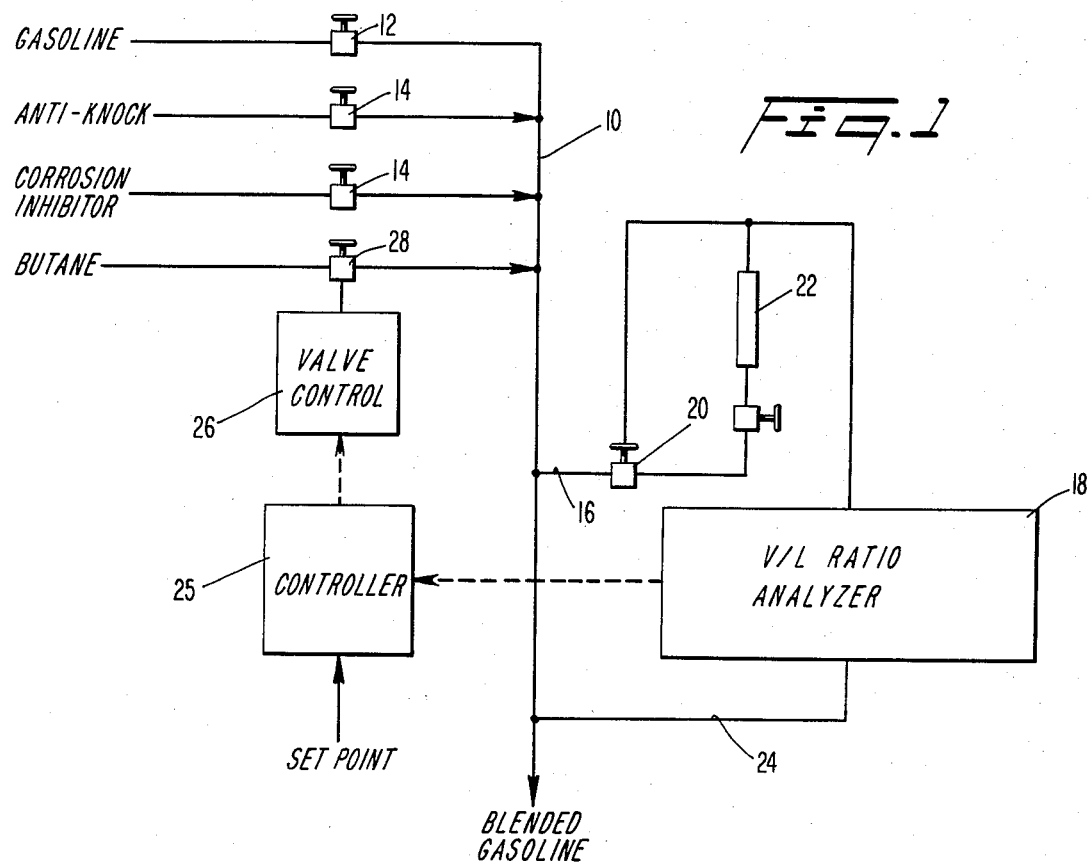
FIG. 1 is a schematic fluid diagram illustrating a gasoline blending system incorporating a vapor-liquid ratio analyzer.

FIG. 1 schematically illustrates a typical environment in which a vapor-liquid ratio analyzer might be used. Gasoline stock, for example that produced in a refinery, is supplied to a feed line 10 through a suitable control valve 12. The various additives to be incorporated into the final product are also supplied to the feed line 10 through appropriate flow regulating and check valves 14. These additives can include, for example, an anti-knock fluid, a corrosion inhibitor, and other well known liquids. In addition, butane is added to the blended gasoline to increase its volatility and reduce the net cost of the final product. The blended gasoline that results from the addition of these various additives is supplied to storage tanks or suitable transport vehicles.

A sampling line 16 is connected to the feed line 10 downstream from the point at which the last additive is supplied to the feed line. The sampling line diverts a small flow of the blended gasoline to a vapor-liquid ratio analyzer 18. The flow of the sample can be regulated by a suitable pressure control valve 20, and any residue therein can be removed by an in-line filter 22. After being tested for its vapor-liquid ratio, the sampled fluid is returned to the feed line 10 through a line 24.

The analyzer 18 produces an output signal related to the measured vapor-liquid ratio temperature of the sampled fluid for a specified ratio. This output signal can be fed to a feedback controller 25 which compares the analyzer signal to a specified set point, e.g. a desired V/L temperature. Any difference between the two compared values is fed as a control signal to a valve control circuit 26, which actuates a flow regulating valve 28 to control the amount of butane that is supplied to the feed line 10. Thus, the amount of butane supplied to the feed line 10 is regulated in accordance with the measured vapor-liquid ratio temperature of the blended gasoline, to maintain this temperature at a desired value.

The valve control circuit 26 and flow regulating valve 28 can be any suitable conventional type of valve that is opened and closed in response to an electrical, hydraulic or pneumatic signal. In addition the feedback controller can be any suitable control circuit that produces an appropriate output signal related to the difference between the measured and set-point values.

Figure 2:
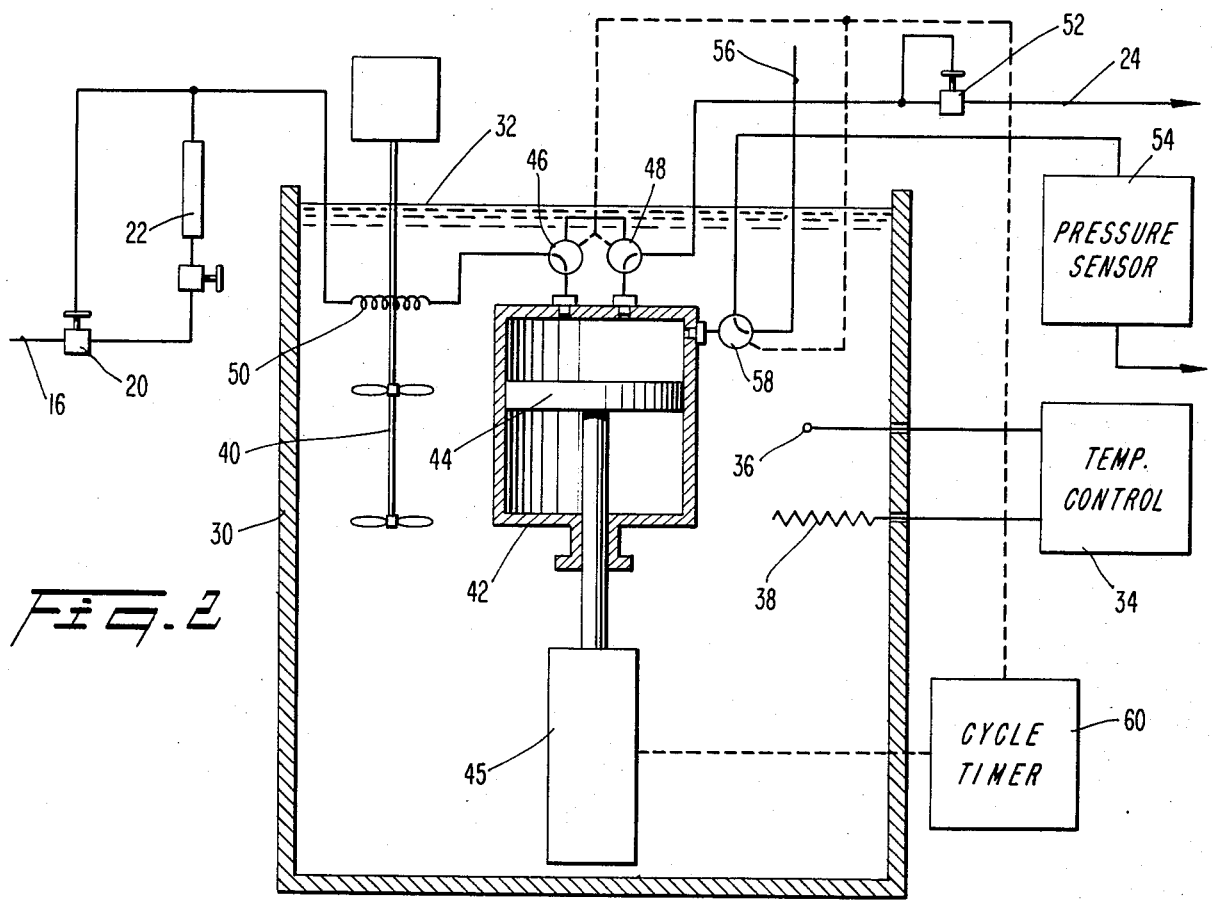
FIG. 2 is a side view, partly in section, of a vapor-liquid ratio analyzer constructed in accordance with the present invention.

Referring now to FIG. 2, an embodiment of a vapor-liquid ratio analyzer that is constructed in accordance with the present invention and that can be used in the blending system of FIG. 1 comprises a tank 30 containing a temperature-controlled bath 32. The bath 32 can be water, for example, or any other suitable liquid medium. The temperature of the bath is regulated by a suitable temperature control mechanism 34 which includes a temperature sensing device 36, for example a thermocouple probe, and a heating element 38, such as an electric resistance heater or the like. The temperature of the bath that is established by the temperature control 34 is preferably variable to adjust the vapor-liquid ratio temperature for different blends of gasoline. Uniformity of the bath temperature is maintained by a suitable agitating mechanism 40, such as a propeller stirring device or the like.

Submersed within the bath 32 is a chamber 42 having a linearly reciprocal piston 44 disposed therein. Linear translation of the piston 44 is provided by a suitable hydraulic or pneumatic cylinder 45 that can be mounted either within or outside of the container 30.

The sample of the blended gasoline flowing in the sampling line 16 is normally diverted through the chamber 42 by means of a pair of 3-way valves 46 and 48. Prior to the time that the sampled liquid flows into the chamber 42 it passes through a heat exchanger coil 50 so that it is brought to the same temperature as the bath 32. A pressure control valve 52 is disposed in the sample return line 24 to maintain the sample flowing through the chamber at a suitable pressure.

Also connected to the chamber 42, so as to be in selective communication with the fluid within the chamber, is an absolute pressure sensing device 54. The pressure sensor 54 is normally connected to atmospheric pressure through a vent line 56. However, selective communication of the pressure sensor with the interior of the chamber 42 is provided by means of a three-way valve 58.

The operation of the analyzer illustrated in FIG. 2, to determine the vapor-liquid ratio temperature of a sample of blended gasoline, is best understood with reference to the sequence of operations illustrated in FIGS. 3A–3F. In the situation illustrated in FIG. 3A, the three-way valves are in their normal positions so that the valve 46 allows the sample liquid in the line 16 to flow into the chamber 42 and the valve 48 enables excess liquid to flow out of the chamber and into the return line 24. At this time, the valve 58 connects the pressure sensor 54 to the vent line 56, to isolate the sensor from the system pressure. When it is desired to analyze a sample of the liquid, the cylinder 45 is actuated to raise the piston 44 to the position shown in FIG. 3B. This operation expells excess liquid and any vapors from the chamber 42.

The top position of the piston 44 is precisely determined so that a specified unit volume of liquid is contained within the chamber. When the piston reaches this point, the sample diverting valves 46 and 48 are actuated, as illustrated in FIG. 3C, closing the chamber to trap the specified volume of liquid and divert the flow of fluid around the chamber 42. The cylinder 46 is then actuated to lower the piston 44 and thereby expand the volume of the chamber 42 (FIG. 3D). The extent to which the volume of the chamber is multiplied through the lowering of the piston is determined in accordance with the desired vapor-liquid ratio of the gasoline. For example, if the desired ratio is 20, the piston 44 travels an amount necessary to increase the volume of the chamber 42 to be twenty-one times the unit volume provided when the piston was at its uppermost position illustrated in FIGS. 3B and 3C. As a result of this increase in the available capacity of the chamber, some of the liquid sample trapped therein evaporates into the newly created space, generating twenty unit volumes of vapor.

Since the chamber 42 is submerged within the bath 30, the temperature of the liquid and vapor within the chamber will eventually be the same as the bath temperature. In order to increase the rate at which uniformity of temperature is established, agitation can be applied to the contents of the chamber. For example, the entire chamber could be shaken by any suitable mechanism (not shown).

After a vapor-liquid equilibrium is established, i.e. when the amount of evaporating liquid is equal to the amount of condensing vapor, the sampling valve 58 is actuated to place the pressure sensor 54 in fluid communication with the interior of the chamber 42 (FIG. 3E). The pressure sensor measures the absolute pressure within the chamber. After the measurement of the pressure is completed, the valves 48 and 58 return to their normal position, and the piston 44 is raised to discharge the vapor from the chamber (FIG. 3F). If desired, the chamber can be flushed with water at this time to purge any residual hydrocarbons that might adversely affect the next measurement. Subsequently, the three-way valve 46 returns to its normal position so that the condition illustrated in FIG. 3A is once again established.

This sequence of operation of the cylinder 45 and the three-way valves 46, 48 and 58 to carry out the preceding cycle of steps can be automatically controlled by a timing circuit 60. The timer can also control the shaking mechanism, if one is provided.

The absolute pressure of the vapor and liquid within the chamber after the equilibrium condition is established provides an indication of the V/L temperature of the gasoline. More specifically, the absolute pressure is compared to a reference pressure, e.g. 14.70 psia. If the measured pressure is the same as the reference pressure, the vapor-liquid ratio temperature of the gasoline is the same as the bath temperature. Any deviations of the absolute measured pressure from the reference pressure are directly proportional to the difference between the V/L temperature and the bath temperature. More specifically, each 0.2 psi difference between the measured and reference pressures translates into 1° F. deviation from the bath temperature. Thus, the vapor-liquid ratio temperature can be computed according to the following formula:

$$T_{V/L} = T_B + [(P_{ref} - P_{abs})/0.2 \text{ psi}]$$

where, $T_{V/L}$ is the vapor-liquid ratio temperature, $T_B$ is the temperature of the bath 32, $P_{ref}$ is the reference pressure (psia), and $P_{abs}$ is the absolute (measured) pressure of the contents of the chamber 42.

Thus, the output signal from the pressure sensor 54, which can be either the absolute measured pressure or the deviation of this measured pressure from the reference pressure, can be supplied to a suitable indicator to provide a display of the vapor-liquid ratio temperature. For example it could be fed to a meter calibrated in units of temperature to indicate the deviation of the vapor-liquid ratio temperature from the bath temperature. Alternatively, this output signal can be directly applied to the feedback controller 25 illustrated in FIG. 1, to adjust the flow of butane that is being mixed with the blended gasoline, and thereby maintain the V/L temperature at the desired value. For example, the feedback controller 25 might comprise a bridge circuit that is in a null condition when the measured pressure is the same as the reference pressure. Deviations of the measured pressure from the reference pressure will cause the bridge circuit to provide an electrical signal that can be used to adjust the valve 28, for example through a motor (not shown).

As an alternative to the expansible chamber illustrated in FIGS. 2 and 3A-3F, it is also possible to generate the required vapor volume using a chamber having a fixed capacity. Such an alternative approach is schematically illustrated in FIGS. 4A-4D. In this embodiment, the liquid in the sample line 16 normally flows through a bypass loop 60 under the control of a three-way valve 62. When it is desired to measure the V/L temperature of the gasoline, a fixed volume chamber 64 is connected to a vacuum source by means of a two-way valve 66 to evacuate any fluids therein, as illustrated in FIG. 4A.

Once the chamber 64 is evacuated, the valve 66 is closed, a two-way valve 68 in the sample line 16 is closed and the three-way valve 62 is actuated to dispense a predetermined volume of the liquid into the chamber 64 (FIG. 4B). The volume that is dispensed is determined by the capacity of the flow line 70 between the valves 62 and 68, and is a fraction of the capacity of the chamber 64 in accordance with the desired vapor-liquid ratio. For example, if the vapor-liquid ratio is 20, the capacity of the flow line 70 is 1/21 that of the chamber 64. The chamber 64 is immersed in a temperature-controlled bath, and can be shaken or otherwise agitated to quickly bring the temperature of the liquid sample, and the vapor produced thereby, to that of the bath.

The pressure sensor 54 continuously measures the pressure within the chamber 64. Once vapor-liquid equilibrium is established at the desired temperature, this pressure reading can be used to determine the vapor-liquid ratio temperature in the same manner as in the previously discussed embodiment. At other times during the measuring cycle, the pressure reading could be used for calibration or diagnostic purposes, or it might be used to inhibit actuation of the valves 62, 64 and 68 until the vacuum within the chamber 64 is at a sufficient level.

After the pressure measurement is taken, the valves 62 and 68 are actuated as shown in FIG. 4C to cause the sample liquid to flow through the bypass loop 60, and the chamber 64 is opened to a drain by means of a two-way valve 72, to discharge the gasoline sample. In addition, the chamber is flushed with water supplied through a three-way valve 74 and a two-way flow control valve 76. Subsequently, pressurized air is introduced into the chamber by means of the three-way valve 74 to partially dry the chamber before evacuation to test the next sample (FIG. 4D). The system is then ready to return to the condition illustrated in FIG. 4A.

As in the embodiment of FIG. 2, the operation of the various valves to evacuate the chamber 64, introduce the sample fluid, measure the pressure, and drain, flush and dry the chamber can be automatically controlled by means of a suitable timer. Similarly, the sample input line can be provided with suitable filters and flow control valves, and have a heat exchanger coil submersed in the bath to bring the sample liquid up to bath temperature.

From the foregoing, it will be appreciated that the present invention provides a simple yet reliable system for measuring the vapor-liquid ratio of a liquid product. Although the measurement of the volatility of the product by measuring pressure at a given vapor-liquid ratio and temperature may initially seem to be an indirect approach, in fact it is as valid as the two most apparent alternatives, i.e. measuring the vapor-liquid ratio at a specified temperature and pressure, or measuring the temperature at a specified vapor-liquid ratio and pressure. The components that comprise the system are relatively few in number and readily available, and at the same time are simple enough that reliability does not present a significant problem. In this regard, the size of the structure can be as large as is convenient to provide the desired degree of ruggedness.

It will be appreciated by those of ordinary skill in the art that the present invention can be embodied in other specific forms without departing from the spirit or essential characteristics thereof. For example, although it has been described in terms of the in-line measurement of gasoline volatility, it is also suitable for use in off-line, e.g. laboratory, applications. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. A method for measuring the vapor-liquid temperature of a liquid for a specified vapor-liquid ratio, comprising the steps of:
    filling a chamber with a unit volume of the liquid;
    expanding the chamber to create a volume which is a predetermined fixed multiple of said unit volume, enabling some of the liquid to evaporate into the expanded volume;
    maintaining the liquid and vapor at a predetermined temperature;
    measuring the pressure within the chamber after vapor-liquid equilibrium is established;
    determining the difference between the measured pressure and a reference pressure; and
    deriving the vapor-liquid ratio temperature from the determined pressure differential.

2. The method of claim 1 wherein said fixed multiple is equal to the specified vapor-liquid ratio for the liquid at said predetermined temperature and said reference pressure.

3. The method of claim 1 wherein said chamber is submersed in a bath maintained at said predetermined temperature.

4. A method for measuring the vapor-liquid ratio temperature of a liquid, comprising the steps of:
    discharging a fixed volume of the liquid into a chamber having a capacity which is a predetermined multiple of said fixed volume, said multiple being related to a desired vapor-liquid ratio at a specified temperature;
    maintaining said liquid, and any vapor which evaporates therefrom into said chamber, at a predetermined temperature that is related to said specified temperature;
    measuring the pressure within said chamber; and
    determining the vapor-liquid ratio temperature from said predetermied temperature, based upon the difference between the measured pressure and a reference pressure.

5. The method of claim 4 wherein said step of discharging comprises filling a chamber having a volume equal to said fixed volume, and then expanding the capacity of the chamber to said predetermined multiple volume.

6. The method of claim 4 wherein the capacity of said chamber is fixed, and further including the step of evacuating said chamber prior to said discharging step.

7. The method of claim 4 wherein said chamber is submersed in a bath maintained at said specified temperature.

8. The method of claim 4 further including the step of flushing said chamber after said measuring step.

9. A method for controlling the addition of a volatile liquid to a blended product, comprising the steps of:
    discharging a unit volume sample of the blended product into an enclosed chamber having a capacity which is a predetermined multiple of said unit volume, said multiple being related to a desired vapor-liquid ratio for the blended product at a specified temperature and pressure;
    maintaining the temperature of fluids in said chamber at said specified temperature;
    measuring the pressure within said chamber;
    determining the difference between the measured pressure and said specified pressure; and
    regulating the rate at which the volatile liquid is added to the blended liquid product in accordance with said difference.

10. The method of claim 9 wherein said chamber is expansible and said step of discharging includes filling said chamber while the volume of said chamber is equal to said unit volume, and further including the step of expanding the volume of said chamber from said unit volume to said multiple unit volume subsequent to said discharging step.

11. The method of claim 9 wherein the capacity of said chamber is fixed, and further including the step of evacuating said chamber prior to said discharging step.

12. Apparatus for controlling the proportion of a volatile liquid in a blended liquid product to thereby regulate the volatility of the blended product, comprising:

an enclosed chamber;

means for maintaining the temperature of said chamber at a specified value;

means for introducing a predetermined volume of a sample of the liquid product into said chamber and for enabling said sample to evaporate into a fixed volume which is a specified multiple of said predetermined volume;

a pressure sensor for measuring the pressure of the contents of said chamber;

means for mixing a volatile liquid with the blended liquid product; and a valve that is operated in response to said pressure sensor for controlling the rate at which the volatile liquid is added to the blended product by said mixing means.

13. The apparatus of claim 12 wherein said temperature maintaining means comprises a liquid bath in which said chamber is immersed.

14. The apparatus of claim 12 wherein said chamber is expansible, and said enabling means includes means for expanding the volume of said chamber from said predetermined volume to said fixed volume.

15. The apparatus of claim 14 wherein said introducing means includes a pair of three-way sample diverting valves.

16. The apparatus of claim 15 wherein said expansible chamber includes a translatable piston, and further including a cycle timer for automatically providing coordinated actuation of said sample diverting valves and said piston to carry out a volatility measurement.

17. The apparatus of claim 16 further including a valve for selectively connecting said pressure sensor with the interior of said chamber, said valve also being controlled by said timer.

18. The apparatus of claim 12 wherein said chamber has a fixed capacity, and wherein said enabling means includes means for evacuating said chamber.

19. The apparatus of claim 12 further including means to flush said chamber and thereby purge it of residual sample liquid.

20. A method for controlling the addition of a volatile liquid to a second liquid to produce a blended product having a predetermined vapor-liquid ratio at a specified temperature and pressure, comprising the steps of:

generating a volume of vapor from a predetermined volume of the blended product, said vapor volume being a multiple of said predetermined volume which multiple is related to said predetermined ratio;

maintaining the volumes of vapor and liquid at said specified temperature;

measuring the absolute pressure of said vapor volume when an equilibrium condition is established; and regulating the proportion of said volatile liquid that is added to said second liquid in accordance with the difference between the measured pressure and said specified pressure.

21. The method of claim 20 further including the step of determining the vapor-liquid ratio temperature of the blended product from said difference.

* * * * *